US011725646B2

(12) United States Patent
Tanaka (10) Patent No.: US 11,725,646 B2
(45) Date of Patent: Aug. 15, 2023

(54) FLUID CONTROL DEVICE

(71) Applicant: Murata Manufacturing Co., Ltd., Kyoto (JP)

(72) Inventor: Nobuhira Tanaka, Kyoto (JP)

(73) Assignee: MURATA MANUFACTURING CO., LTD., Kyoto (JP)

(*) Notice: Subject to any disclaimer, the term of this patent is extended or adjusted under 35 U.S.C. 154(b) by 423 days.

(21) Appl. No.: 16/991,403

(22) Filed: Aug. 12, 2020

(65) Prior Publication Data

US 2020/0370544 A1 Nov. 26, 2020

Related U.S. Application Data

(63) Continuation of application No. PCT/JP2018/041454, filed on Nov. 8, 2018.

(30) Foreign Application Priority Data

Feb. 13, 2018 (JP) .................. 2018-022713

(51) Int. Cl.
*F04B 17/00* (2006.01)
*F04B 45/047* (2006.01)
(Continued)

(52) U.S. Cl.
CPC .......... *F04B 45/047* (2013.01); *F04B 17/003* (2013.01); *A61B 5/021* (2013.01);
(Continued)

(58) Field of Classification Search
CPC ........ F04B 17/00; F04B 54/047; A61B 5/021; A61B 2017/00402; A61B 2217/005;
(Continued)

(56) References Cited

U.S. PATENT DOCUMENTS

2014/0017093 A1* 1/2014 Locke .................. F04B 19/006
417/32
2015/0040904 A1* 2/2015 Nitta .................... A61M 16/205
128/204.23
(Continued)

FOREIGN PATENT DOCUMENTS

| JP | 2015522123 A | 8/2015 |
| WO | 2015125608 A1 | 8/2015 |
| WO | 2016181833 A1 | 11/2016 |

OTHER PUBLICATIONS

International Search Report issued in Application No. PCT/JP2018/041454, dated Jan. 22, 2019.
(Continued)

*Primary Examiner* — Connor J Tremarche
(74) *Attorney, Agent, or Firm* — Pearne & Gordon LLP (57) ABSTRACT

A fluid control device includes a housing. The housing includes a first main plate, a second main plate, and a side plate connecting the first main plate and the second main plate. The housing has a pump chamber defined by the first main plate, the second main plate, and the side plate. The fluid control device also includes a driver, a first hole that extends through the first main plate or the second main plate, and a first recess formed in the first main plate between a center and a circumference or the second main plate between a center and a circumference.

20 Claims, 9 Drawing Sheets

(51) Int. Cl.
  *A61B 5/021* (2006.01)
  *A61B 17/00* (2006.01)
  *A61H 9/00* (2006.01)
  *A61M 16/14* (2006.01)
  *A61M 1/00* (2006.01)

(52) U.S. Cl.
  CPC ............... *A61B 2017/00402* (2013.01); *A61B 2217/005* (2013.01); *A61H 9/00* (2013.01); *A61M 1/90* (2021.05); *A61M 16/14* (2013.01); *A61M 2205/0294* (2013.01)

(58) Field of Classification Search
  CPC . A61H 9/00; A61M 16/14; A61M 2205/0294; A61M 1/90
  See application file for complete search history.

(56) References Cited

U.S. PATENT DOCUMENTS

2016/0348666 A1\* 12/2016 Tanaka .................. F04B 45/047
2018/0051686 A1    2/2018 Tanaka et al.

OTHER PUBLICATIONS

Written Opinion issued in Application No. PCT/JP2018/041454, dated Jan. 22, 2019.

\* cited by examiner

FLUID CONTROL DEVICE

This is a continuation of International Application No. PCT/JP2018/041454 filed on Nov. 8, 2018 which claims priority from Japanese Patent Application No. 2018-022713 filed on Feb. 13, 2018. The contents of these applications are incorporated herein by reference in their entireties.

BACKGROUND

Technical Field

The present disclosure relates to a fluid control device including a driver formed from, for example, a piezoelectric element.

Various types of a fluid control device, such as a pump, including a driver formed from a piezoelectric element or other devices have been commercially available.

Patent Document 1 discloses a pump that forms the antinodes of vibrations at the middle between the center of the pump and the connection portion of the pump. The pump includes a vibration plate and a top plate disposed close to each other.

Patent Document 1: International Publication No. 2015/125608

BRIEF SUMMARY

In the pump with the structure described in Patent Document 1, when increasing the amplitude, the vibration plate would come closer to the top plate at the middle between the center of the pump and the connection portion of the pump, and thus would receive great air resistance. This structure restricts displacement of the vibration plate, and may fail to obtain an intended flow capacity.

The present disclosure thus aims to provide a fluid control device that can efficiently obtain an intended large flow capacity.

A fluid control device according to the present disclosure includes a housing including a first main plate, a second main plate having a first main surface opposing a first main surface of the first main plate, and a side plate that connects the first main plate and the second main plate. The housing has a pump chamber defined by the first main plate, the second main plate, and the side plate. The fluid control device also includes a driver disposed on a main surface of the first main plate to bend and vibrate the first main plate, a first hole that extends through the first main plate from the first main surface to a second main surface, or extends through the second main plate from the first main surface to a second main surface, and a first recess formed in at least one of the first main surface of the first main plate facing the pump chamber between a center and a circumference, and the first main surface of the second main plate facing the pump chamber between a center and a circumference.

In this structure, the first recess reduces air resistance exerted on the first main plate when the first main plate and the second main plate approach, and thus prevents reduction of displacement of the first main plate. Specifically, this structure can obtain a large flow capacity, and improves the performance of a pump.

The fluid control device according to the present disclosure can include a second hole that extends through the first main plate or the second main plate from the first main surface to the second main surface, and a valve disposed at the first hole.

This structure can prevent backflow of a fluid with the valve, and thus has high fluid characteristics and pressure characteristics.

In the fluid control device according to the present disclosure, the first recess can be formed in the first main surface of the first main plate between the driver and the circumference or formed in the first main surface of the second main plate between the driver and the circumference.

This structure thus prevents reduction of displacement in an area of the first main plate over which the first main plate is displaced.

In the fluid control device according to the present disclosure, bending vibrations of the first main plate can have a node of vibrations at a portion between the center and the circumference. The first recess can be formed between the node of vibrations and the circumference when the first main plate or the second main plate is viewed in a plan from the main surface of the first main plate to the main surface of the second main plate.

In this structure, the first recess has a large area. This structure thus has a large effect on reduction of air resistance, and reduces reduction of displacement. Specifically, this structure can increase the flow capacity.

In the fluid control device according to the present disclosure, bending vibrations of the first main plate can have an antinode of vibrations between the node of vibrations and the circumference. The first recess can be formed to overlap the adjacent antinode of vibrations when the first main plate or the second main plate is viewed in a plan from the main surface of the first main plate to the main surface of the second main plate.

In this structure, the first recess is formed at a portion having a large displacement, such as the position of the antinode of bending vibrations. This structure thus has a higher effect on reduction of air resistance, and further reduces reduction of displacement of the first main plate. Specifically, this structure can increase the flow capacity.

In the fluid control device according to the present disclosure, the first hole can be disposed to overlap the first recess when viewed in a plan from the main surface of the first main plate to the main surface of the second main plate.

This structure can further increase displacement of the first main plate, and further increase the flow capacity.

In the fluid control device according to the present disclosure, the first hole can be formed in the main surface of the first main plate or the second main plate facing the first recess.

This structure can further increase displacement of the first main plate, and further increase the flow capacity.

In the fluid control device according to the present disclosure, the first recess can be formed in the second main plate.

This structure can further increase displacement of the first main plate, and further increase the flow capacity.

In the fluid control device according to the present disclosure, the first recess can be annularly formed in the first main plate or the second main plate when viewed in a plan from the main surface of the first main plate to the main surface of the second main plate.

In this structure, the first main plate or the second main plate in the fluid control device can be uniformly displaced in all the directions. Specifically, the fluid control device improves its efficiency.

In the fluid control device according to the present disclosure, the first recess can be formed in a full circle in the first main plate or the second main plate.

In this structure, the first main plate or the second main plate in the fluid control device can be uniformly displaced in all the directions. Specifically, the fluid control device improves its efficiency.

In the fluid control device according to the present disclosure, the second recess can be formed in the first main plate or the second main plate at a position corresponding to a center of the pump chamber.

This structure can further increase displacement of the first main plate, and further increase the flow capacity.

The fluid control device according to the present disclosure can include a second recess formed to overlap the first hole in a plan view.

This structure can further increase displacement of the first main plate, and further increase the flow capacity.

In the fluid control device according to the present disclosure, main surfaces of the first main plate and main surfaces the second main plate can be circular.

In this structure, bending vibrations of the first main plate can be uniformly transferred. Specifically, the fluid control device improves its efficiency.

The fluid control device according to the present disclosure is installed in a medical device for use.

This structure improves the performance of a medical device. Examples of medical devices include a sphygmomanometer, a massage machine, an aspirator, a nebulizer, and, a negative pressure wound therapy device.

The present disclosure can provide a fluid control device that can efficiently obtain an intended large flow capacity.

DETAILED DESCRIPTION

First Embodiment

Figure 1:
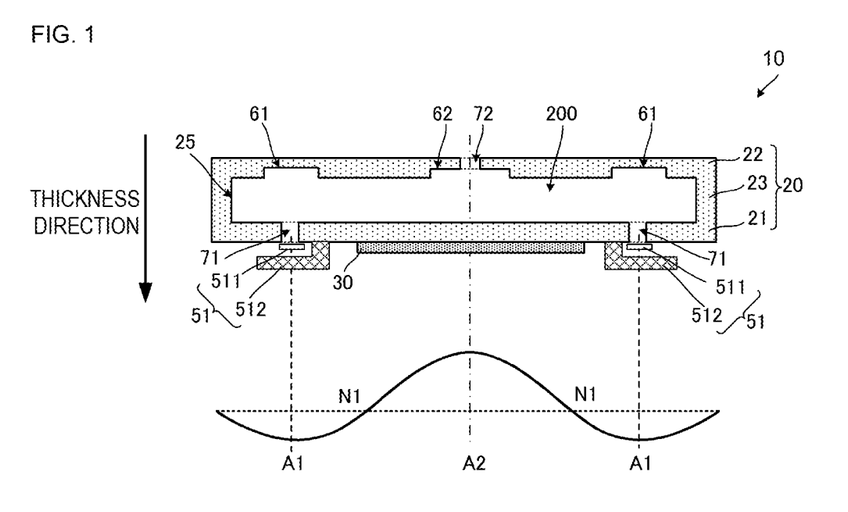
FIG. 1 is a cross-sectional view of a fluid control device 10 according to a first embodiment of the present disclosure, viewed sideways, in a bending vibration state.
Figure 2A:
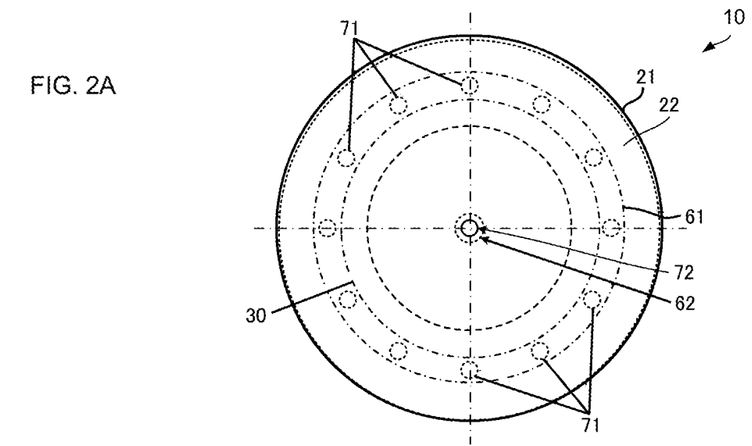
FIG. 2A is a plan view of the fluid control device 10 according to the first embodiment of the present disclosure, viewed from a first main plate 21.
Figure 2B:
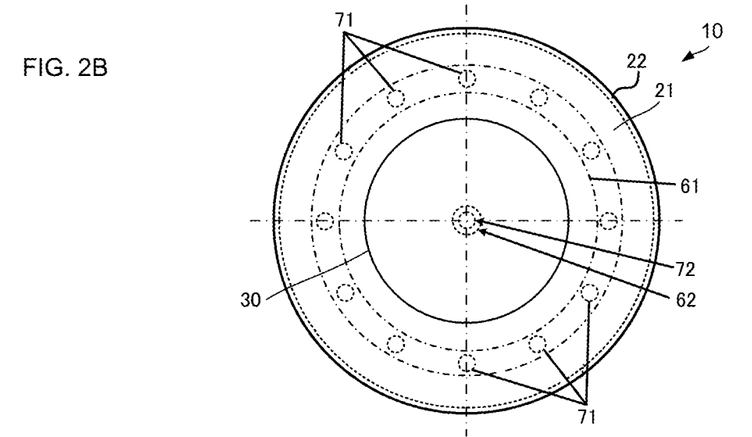
FIG. 2B is a plan view of the fluid control device 10 according to the first embodiment according to the present disclosure, viewed from a second main plate 22.
Figure 3:
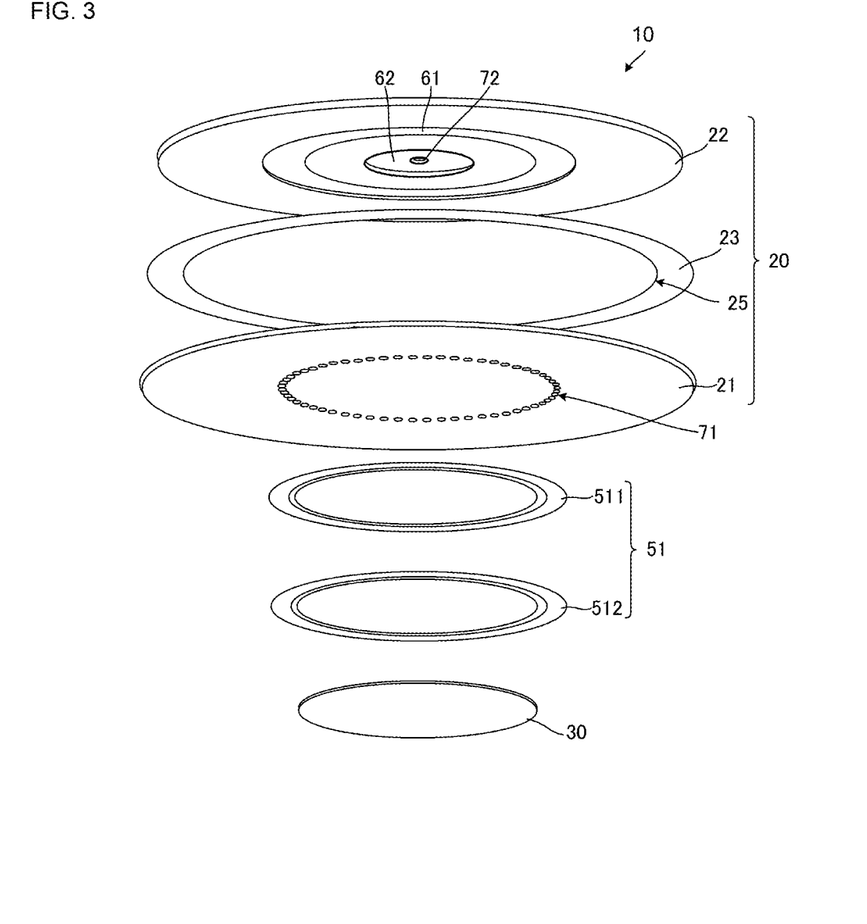
FIG. 3 is an exploded perspective view of the fluid control device 10 according to the present disclosure.
Figure 4A:
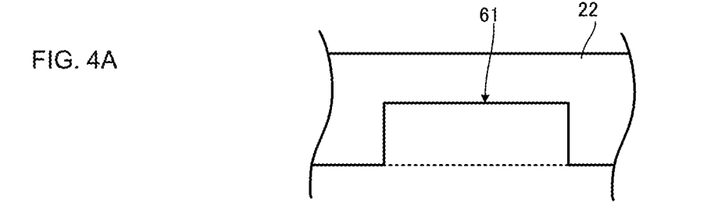
FIG. 4A to FIG. 4C are enlarged views of the shapes of the recess of the fluid control device 10 of the present disclosure.
Figure 4B:
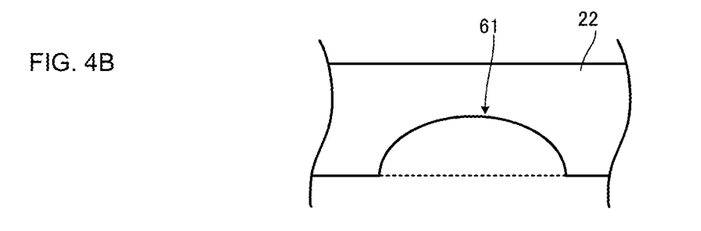
Figure 4C:
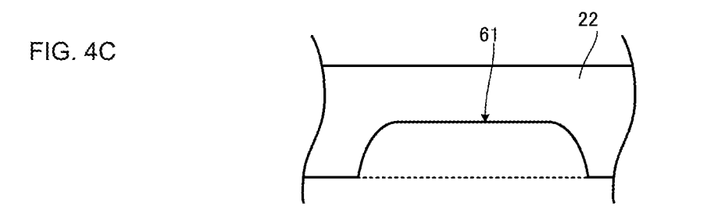
Figure 5:
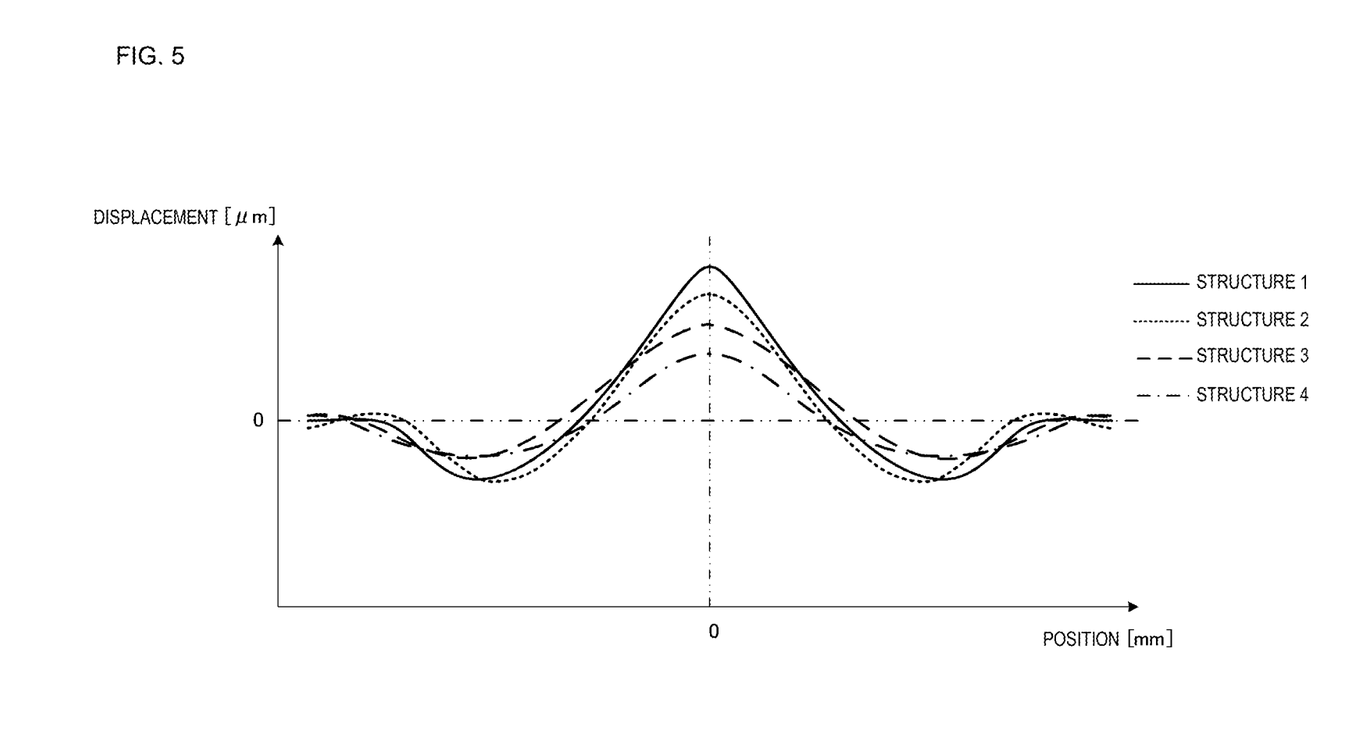
FIG. 5 is a graph of displacement distribution in height of a pump chamber 200 according to the present disclosure.

A fluid control device according to a first embodiment of the present disclosure will be described with reference to the drawings. FIG. 1 is a cross-sectional view of a fluid control device 10 according to a first embodiment of the present disclosure, viewed sideways, in a bending vibration state. FIG. 2A is a plan view of the fluid control device 10 according to the first embodiment of the present disclosure, viewed from near a first main plate 21, and FIG. 2) is a plan view of the fluid control device 10 according to the first embodiment according to the present disclosure, viewed from near a second main plate 22. FIG. 3 is an exploded perspective view of the fluid control device 10 according to the first embodiment of the present disclosure. FIG. 4A to FIG. 4C are enlarged views of the recesses of the fluid control device 10 according to the first embodiment of the present disclosure. FIG. 5 is a graph of displacement distribution in height of the pump chamber 200 according to the present disclosure. For ease of illustration, some reference signs are omitted, and some components are exaggerated.

As shown in FIG. 1, FIG. 2A, FIG. 2B, and FIG. 3, the fluid control device 10 includes a housing 20 and a piezoelectric element 30. The housing 20 includes a first main plate 21, a second main plate 22, and a side plate 23. The piezoelectric element 30 corresponds to "a driver" in the present disclosure. The fluid control device 10 according to the present embodiment is a pump.

The first main plate 21 is formed from a material with a thickness that allows the first main plate 21 to vibrate in a direction orthogonal to the main surface. Examples of the material of the first main plate 21 include stainless steel.

The second main plate 22 is a circular plate. The second main plate 22 may be formed from a material having a predetermined rigidity high enough to function as the housing 20. The second main plate 22 is a circular plate, as in the first main plate 21.

The side plate 23 is a hollow cylinder. The side plate 23 may also be formed from a material having a predetermined rigidity high enough to function as the housing 20.

The side plate 23 is disposed between the first main plate 21 and the second main plate 22 to connect the first main plate 21 and the second main plate 22. More specifically, in a plan view, the first main plate 21 and the second main plate 22 share the same center. The side plate 23 connects circumferences 25 of the first main plate 21 and the second main plate 22 thus arranged, circumferentially throughout. Here, the direction in which the second main plate 22, the side plate 23, and the first main plate 21 are stacked one on the other in order is referred to as a thickness direction.

In this structure, the housing 20 has a pump chamber 200, which is a substantially cylindrical space defined by the first main plate 21, the second main plate 22, and the side plate 23. The pump chamber 200 has a substantially circular cross section when taken by the plate parallel to the first main plate 21. The cross-sectional area may vary in the direction from the first main plate 21 toward the second main plate 22.

The piezoelectric element 30 includes a piezoelectric disk and driver electrodes. The driver electrodes are formed on both main surfaces of the piezoelectric disk.

The piezoelectric element 30 is disposed on the surface of the first main plate 21 facing away from the pump chamber 200, that is, on the outer side of the housing 20. Here, in the plan view, the piezoelectric element 30 and the first main plate 21 substantially share the same center.

The piezoelectric element 30 is connected to a control unit, not illustrated. The control unit generates a driving signal for the piezoelectric element 30, and applies the driving signal to the piezoelectric element 30. The piezoelectric element 30 is displaced with the driving signal, and the displacement causes stress on the first main plate 21. Thus, the first main plate 21 bends and vibrates.

The driving signal expands and contracts the piezoelectric element 30 so that the first main plate 21 causes second order bending vibrations having nodes N1 and antinodes A1 and A2. Specifically, when the first main plate 21 is viewed in a plan, the antinode A2 occurs at the center, and the nodes N1, and then the antinodes A1 occur at positions spaced further toward the circumference 25.

For example, vibrations of the first main plate 21 have a waveform of Bessel functions of the first kind. Thus, the first main plate 21 functions as a vibration plate.

The first main plate 21 of the fluid control device 10 has first holes 71. A valve unit 51 is disposed at the first holes 71 on the side of the first main plate 21 facing away from the pump chamber 200, that is, on the outer side of the housing 20. The second main plate 22 of the fluid control device 10 has a first recess 61, a second recess 62, and a second hole 72. For example, the second main plate 22 has a thickness of approximately 0.3 mm. The valve unit 51 includes a film 511 and a cover 512. The film 511 has a thickness of approximately 5 µm. The film 511 is spaced apart from the first holes 71 when air is ejected through the first holes 71, not to avoid air ejection. The film 511 closes the first holes 71 when air flows in through the first holes 71 to prevent air from flowing into the pump chamber 200.

The first recess 61 is formed in the second main plate 22 facing the pump chamber 200, that is, on the inner side of the housing 20. For example, as illustrated in FIG. 2A, FIG. 2B, and FIG. 3, the first recess 61 has an annular shape with an inside diameter of approximately 5.6 mm and an outside diameter of approximately 7.6 mm with respect to the center of the housing 20. The first recess 61 is formed so that a gap between the first main plate 21 and the second main plate 22 is wider in the first recess 61 than at the portion closer to the center or the circumference 25 than the first recess 61.

Specifically, as illustrated in FIG. 1, the first recess 61 is formed between the center of the housing 20 and the side plate 23 (circumference 25). Here, as illustrated in FIG. 1, the first recess 61 is formed at a position that overlaps the antinodes A1 of bending vibrations.

The first recess 61 forms a portion of the second main plate 22 thinner than the other portion. The thickness of this portion is, for example, approximately 0.15 mm. Specifically, in the second main plate 22 with the above-described thickness, the first recess 61 has a thickness of approximately 0.15 mm.

The second recess 62 is formed in the side of the second main plate 22 facing the pump chamber 200, that is, on the inner side of the housing 20. As illustrated in FIG. 2A and FIG. 2B, the second recess 62 is circular. The second recess 62 and the housing 20 share the same center.

As illustrated in FIG. 1, the second recess 62 is formed at the center portion of the housing 20. The second recess 62 is formed to overlap the antinode A2 of bending vibrations.

The second recess 62 forms a portion of the second main plate 22 thinner than the other portion. The thickness of this portion is, for example, approximately 0.15 mm. Specifically, in the second main plate 22 with the above-described thickness, the second recess 62 has a thickness of approximately 0.15 mm.

The first holes 71 and the second hole 72 serve as ventholes of the fluid control device 10.

The first holes 71 extend through the first main plate 21. The first holes 71 have a radius of approximately 0.5 mm. As illustrated in FIG. 2A and FIG. 2B, the multiple first holes 71 are annularly arranged in the first main plate 21. The first holes 71 are formed at positions overlapping the antinodes A1 and the first recess 61 in a plan view.

The second hole 72 extends through the second main plate 22, and is formed at a position overlapping the second recess 62 in a plan view. The second hole 72 and the second recess 62 share the same center.

The first recess 61 is located closer to the circumference 25 than the piezoelectric element 30. The portion of the first main plate 21 facing the first recess 61 receives small air resistance, and thus has a large curvature of bending vibrations. In the present embodiment, the piezoelectric element 30 does not face the first recess 61, and is thus not deformed with a large curvature. Thus, the piezoelectric element 30 has high durability.

In the present embodiment, the first recess 61 does not overlap the nodes N1. Specifically, the first recess 61 is formed at a portion that is displaced to a large extent. The present embodiment thus has a great effect on reduction of air resistance.

The first recess 61 located closer to the circumference 25 than the nodes N1 has a larger area than in the case where the first recess 61 is located closer to the center than the nodes N1. The present embodiment thus particularly has a great effect on reduction of air resistance.

Thus, the first recess 61 is formed in the first main plate 21 to overlap the antinodes A1, which vibrate to a large extent, in a plan view. Thus, the height of the pump chamber 200 in the thickness direction can be increased in an area where the first main plate 21 is displaced to a large extent due to vibrations.

Thus, air resistance between the first main plate 21 and the second main plate 22 decreases, and reduction of displacement of the first main plate 21 is prevented. This structure can thus increase the flow capacity, and improves the performance of the fluid control device 10.

The second recess 62 having a smaller area than the first recess 61 has a small effect on reduction of air resistance. However, together with the first recess 61, the second recess 62 further reduces air resistance between the first main plate 21 and the second main plate 22 when the fluid control device 10 is operated, and reduction of displacement of the first main plate 21 is further prevented. This structure can thus increase the flow capacity, and improves the performance of the fluid control device 10.

The first holes 71 are arranged to overlap the first recess 61 in a plan view. This structure allows a fluid to flow in to and out of the area that is displaced to a large extent. This structure can thus increase the flow capacity by which the fluid flows in and out through the first holes 71.

The first holes 71 are formed in the surface facing the first recess 61. Thus, reduction in rigidity of the bottom portion of the first recess 61 can be prevented, and displacement reduction due to pressure accompanying air resistance can be prevented.

This structure can increase the flow capacity of the fluid control device 10, and thus improves the flow capacity.

The first recess 61 formed in the second main plate 22 prevents the shape of the first main plate 21 from being affected with manufacturing variation in dimensions of the first recess 61. Thus, the first main plate 21 has small manufacturing variation in frequency of bending vibrations. Thus, the first main plate 21 has stable flow capacity characteristics.

Here, the first holes 71 are arranged in a full circle, with gaps interposed therebetween. Thus, the fluid control device 10 has higher efficiency.

FIG. 4A to FIG. 4C are enlarged cross-sectional views of the first recesses 61, viewed sideways. The first recess 61 illustrated in FIG. 4A has an angular cross section, approximately a rectangular parallelepiped cross section. The first recess 61 illustrated in FIG. 4B has an approximately elliptic cross section. The first recess 61 illustrated in FIG. 4C has a cross section of an approximately rectangular parallelepiped with rounded corners. The first recess 61 of the fluid control device 10 may have any of the shapes illustrated in FIG. 4A to FIG. 4C.

The second recess 62 may also have any of the shapes illustrated in FIG. 4A to FIG. 4C.

FIG. 5 is a graph for comparing, at the center of the housing 20, the displacement in height of the pump chamber 200 of the fluid control device 10 according to the present embodiment with the displacement in height of a pump chamber with an existing structure, different from the structure of the fluid control device 10.

Structure 1 is a structure according to the present embodiment. Structure 2 is a structure according to a second embodiment, described below. Structure 3 is a structure of an existing fluid control device only including the second recess 62. Structure 4 is a structure of an existing fluid control device including neither the first recess 61 nor the second recess 62.

As shown in FIG. 5, the amount of displacement of the antinode A2 at the center is larger than the amount of displacement in an existing structure.

For example, the center of the housing 20 is defined as 0. The pump chamber 200 of Structure 3 has a displacement in height of 7.7 µm. The pump chamber 200 of Structure 4 has a displacement in height of 6.3 µm. The pump chamber 200 of Structure 1 according to the present embodiment has a displacement in height of 12.3 µm. Specifically, as in the present embodiment, the first recess 61 and the second recess 62 can increase the displacement in height of the pump chamber 200, and further increase the flow capacity. As illustrated in Structure 3, the pump chamber 200 has a displacement in height of 7.7 µm, so that the pump chamber 200 increases the displacement compared to an existing structure. However, in Structure 3, which does not have the first recess 61, the pump chamber 200 has a smaller displacement in height than that in Structure 1.

The pump of Structure 1 has characteristics including a flow capacity of 0.7 L/min, and a pressure of 13 kPa. The pump of Structure 3, which is an existing structure, has characteristics including a flow capacity of 0.3 L/min, and a pressure of 5 kPa, which are lower than those in Structure 1.

As described above, the first recess 61 has a width of, for example, approximately 2 mm. However, the first recess 61 may have a width within the range of the following lower and upper limits. The lower limit of the width of the first recess 61 may be twice the minimum value of the height of the pump chamber 200 when the fluid control device 10 is stopped, in other words, twice the minimum value of the gap between the first main plate 21 and the second main plate 22 when the fluid control device 10 is stopped. This structure can reduce air resistance.

The upper limit of the width of the first recess 61 may be larger than or equal to twice the minimum height of the pump chamber 200 at a portion of the pump chamber 200 having a height lower than the average height when the fluid control device 10 is stopped. Thus, air in the pump chamber 200 can be effectively compressed.

This structure can thus increase the flow capacity, and improves the characteristics of the fluid control device 10.

The second hole 72 is formed at a position overlapping the antinode A2. This structure reduces air resistance between the first main plate 21 and the second main plate 22, and thus prevents reduction of displacement of the first main plate 21.

The first recess 61 is formed in a full circle with a uniform width in the fluid control device 10. However, the first recess 61 may be formed in part of the fluid control device 10. Nevertheless, the first recess 61 formed in a full circle in the fluid control device 10 forms no variation between the directions, and improves the efficiency.

In the above structure, the mode of the bending vibrations has been described as second order vibrations. However, the mode may be second or larger order vibrations. Such a structure, for example, where the recess and the antinode overlap each other can also increase the flow capacity.

Second Embodiment

Figure 6:
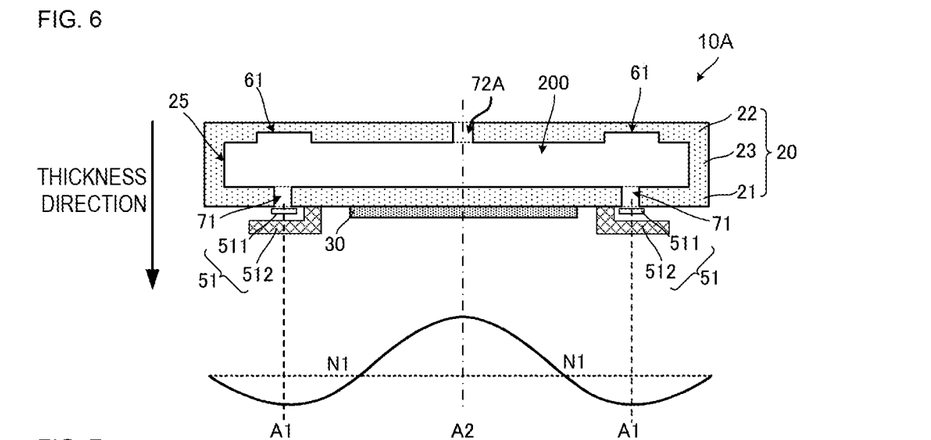
FIG. 6 is a cross-sectional view of a fluid control device 10A according to a second embodiment of the present disclosure, viewed sideways, in a bending vibration state.

A fluid control device according to a second embodiment of the present disclosure will be described with reference to the drawings. FIG. 6 is a cross-sectional view of the fluid control device 10A according to a second embodiment of the present disclosure, viewed sideways. For ease of illustration, some reference signs are omitted, and some components are exaggerated.

As shown in FIG. 6, the fluid control device 10A according to the second embodiment differs from the fluid control device 10 according to the first embodiment in that the fluid control device 10A does not have the second recess 62, and, has a second hole 72A with a shape different from that of the corresponding hole according to the first embodiment. Other components of the fluid control device 10A are the same as those of the fluid control device 10, and will not be described. The fluid control device 10A according to the present embodiment is a pump.

The second hole 72A extends through the second main plate 22. The second hole 72A and the housing 20 share the same center.

The first recess 61 is formed to overlap the antinodes A1 of the first main plate 21, which vibrate to a large extent, in a plan view. Thus, the pump chamber 200 can increase the height in the thickness direction. Specifically, this structure can prevent the first main plate 21 and the second main plate 22 from approaching each other when the fluid control device 10A is in operation.

As illustrated in FIG. 5, Structure 2 corresponds to a structure according to the present embodiment. The fluid control device 10A, which has Structure 2, is compared with Structure 3 and Structure 4, which are existing structures described above.

As illustrated in FIG. 5, the amount of displacement of the antinode A2 at the center is larger than the amount of displacement in an existing structure.

For example, the pump chamber 200 of Structure 3 has a displacement in height of 7.7 μm. The pump chamber 200 of Structure 4 has a displacement in height of 6.3 μm. The pump chamber 200 of Structure 2, which is the present embodiment, has a displacement in height of 11.1 μm. Specifically, as in the present embodiment, the first recess 61 and the second recess 62 can increase the displacement in height of the pump chamber 200, and thus can increase the flow capacity. As illustrated in Structure 3, the pump chamber 200 has a displacement in height of 7.7 μm, which is larger than the displacement of the pump chamber 200 of an existing structure. However, Structure 3, which does not have the first recess 61, has a smaller displacement in height of the pump chamber 200 than in Structure 2.

As described above, air resistance between the first main plate 21 and the second main plate 22 decreases, and displacement of the first main plate 21 increases. Specifically, air in the pump chamber 200 can be effectively compressed, and air resistance can be reduced. This structure can thus increase the flow capacity, and improves the characteristics of the fluid control device 10A.

The present embodiment does not include the second recess 62, so that the center portion of the piezoelectric element 30 is not deformed with a large curvature. Thus, the piezoelectric element 30 has higher durability.

Third Embodiment

Figure 7:
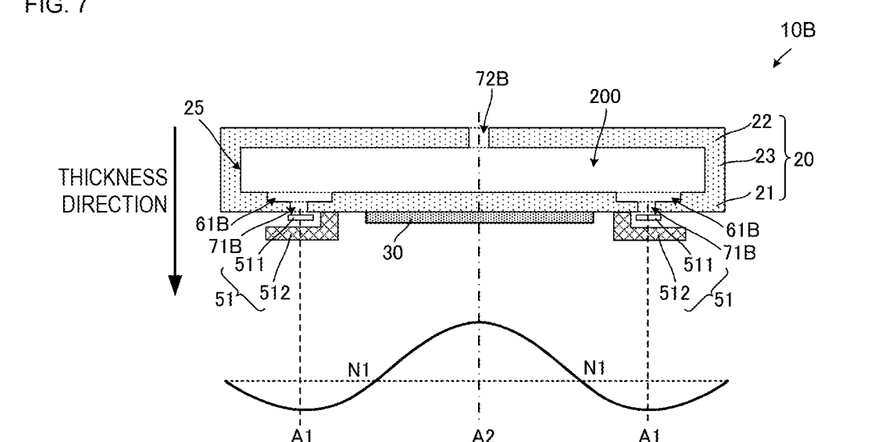
FIG. 7 is a cross-sectional view of a fluid control device 10B according to a third embodiment of the present disclosure, viewed sideways, in a bending vibration state.

A fluid control device according to a third embodiment of the present disclosure will be described with reference to the drawings. FIG. 7 is a cross-sectional view of a fluid control device 10B according to the third embodiment of the present disclosure, viewed sideways. For ease of illustration, some reference signs are omitted, and some components are exaggerated.

As shown in FIG. 7, the fluid control device 10B according to the third embodiment differs from the fluid control device 10 according to the first embodiment in that a first recess 61B is formed in the first main plate 21, the fluid control device 10B does not include the second recess 62, and, first holes 71B and second hole 72B have shapes different from those of the corresponding holes according to the first embodiment. Other components of the fluid control device 10B are the same as those of the fluid control device 10, and will not be described. The fluid control device 10B according to the present embodiment is a pump.

The first recess 61B is formed in the side of the first main plate 21 facing the pump chamber 200, that is, on the inner side of the housing 20.

As illustrated in FIG. 7, the first recess 61B is formed between the center of the housing 20 and the side plate 23 (circumference 25) to overlap the antinodes A1 of bending vibrations in a plan view. The first recess 61B is formed so that a gap between the first main plate 21 and the second main plate 22 is wider in the first recess 61B than at the portion closer to the center or the circumference 25 than the first recess 61B.

The first holes 71B extend through the first main plate 21. The first holes 71B are formed to overlap the first recess 61B in a plan view. Each of the first holes 71B and the first recess 61B share the same center. The multiple first holes 71B are annularly arranged in the first main plate 21.

The second hole 72B extends through the second main plate 22.

As described above, the first recess 61B is formed to overlap the antinodes A1 of the first main plate 21, which vibrate to a large extent, in a plan view. Thus, the height of the pump chamber 200 in the thickness direction can be increased in an area where the first main plate 21 displaces to a large extent due to vibrations. Specifically, this structure can prevent the first main plate 21 and the second main plate 22 from approaching when the fluid control device 10B is in operation.

Thus, air resistance between the first main plate 21 and the second main plate 22 decreases, and displacement of the first main plate 21 increases. This structure can thus increase the flow capacity, and improves the performance of the fluid control device 10B.

Fourth Embodiment

Figure 8:
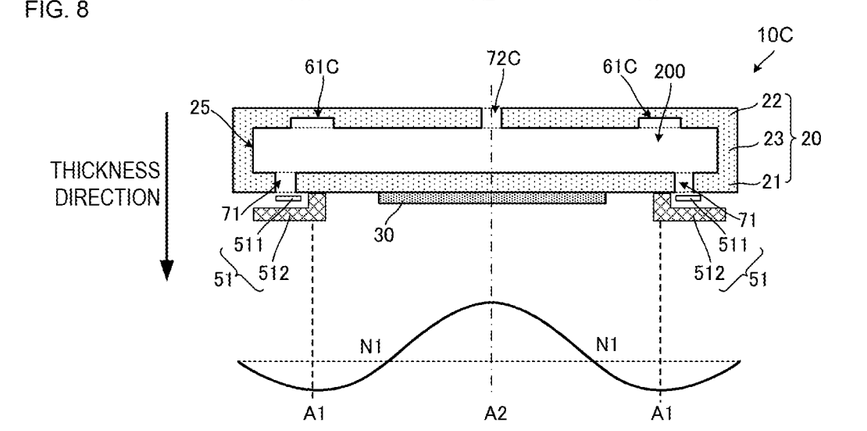
FIG. 8 is a cross-sectional view of a fluid control device 10C according to a fourth embodiment of the present disclosure, viewed sideways, in a bending vibration state.

A fluid control device according to a fourth embodiment of the present disclosure will be described with reference to the drawings. FIG. 8 is a cross-sectional view of a fluid control device 10C according to the fourth embodiment of the present disclosure, viewed sideways. For ease of illustration, some reference signs are omitted, and some components are exaggerated.

As illustrated in FIG. 8, the fluid control device 10C according to the fourth embodiment differs from the fluid control device 10 according to the first embodiment in that a first recess 61C is formed at a position different from that of the corresponding recess according to the first embodiment, the fluid control device 10C does not have the second recess 62, and a second hole 72C has a shape different from that of the corresponding hole according to the first embodiment. Other components of the fluid control device 10C are the same as those of the fluid control device 10, and will not be described. The fluid control device 10C according to the present embodiment is a pump.

The second hole 72C extends through the second main plate 22. The second hole 72C and the housing 20 share the same center.

The first recess 61C is formed to overlap the antinodes A1, which vibrate to a large extent, in a plan view. The first recess 61C and the first holes 71 do not oppose each other. Specifically, the first holes 71 are formed between the first recess 61C and the circumference 25 in a plan view.

Also in this structure, the height of the pump chamber 200 in the thickness direction can be increased. Specifically, this structure can prevent the first main plate 21 and the second main plate 22 from approaching when the fluid control device 10C is in operation.

Thus, air resistance between the first main plate 21 and the second main plate 22 decreases, and reduction of displacement of the first main plate 21 is prevented. This structure can thus increase the flow capacity, and improves the performance of the fluid control device 10C.

Fifth Embodiment

Figure 9:
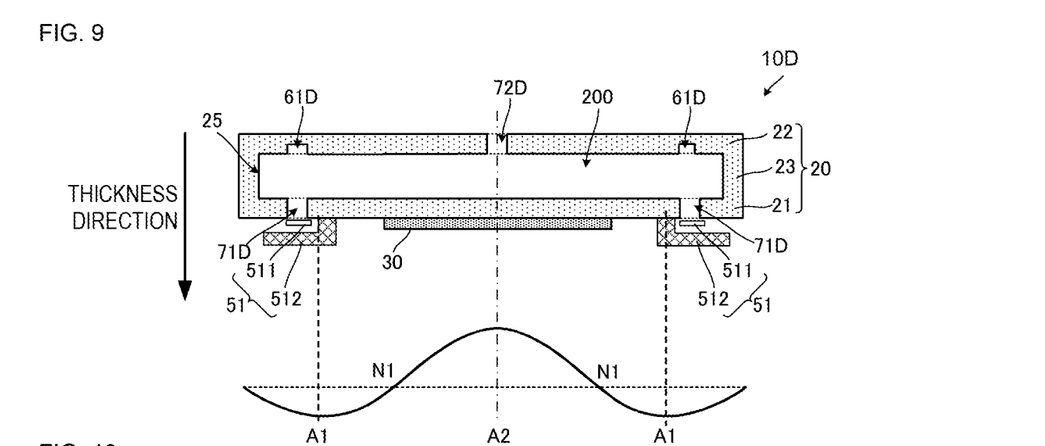
FIG. 9 is a cross-sectional view of a fluid control device 10D according to a fifth embodiment of the present disclosure, viewed sideways, in a bending vibration state.

A fluid control device according to a fifth embodiment of the present disclosure will be described with reference to the drawings. FIG. 9 is a cross-sectional view of a fluid control device 10D according to the fifth embodiment of the present disclosure, viewed sideways. For ease of illustration, some reference signs are omitted, and some components are exaggerated.

As illustrated in FIG. 9, the fluid control device 10D according to the fifth embodiment differs from the fluid control device 10 according to the first embodiment in that a first recess 61D is formed at a position different from that of the corresponding recess according to the first embodiment, the fluid control device 10D does not include the second recess 62, first holes 71D have a shape different from that of the corresponding holes according to the first embodiment, and a second hole 72D is formed at a position different from that of the corresponding hole according to the first embodiment. Other components of the fluid control device 10D are the same as those of the fluid control device 10, and will not be described. The fluid control device 10D according to the present embodiment is a pump.

The second hole 72D extends through the second main plate 22. The second hole 72D and the housing 20 share the same center.

The first recess 61D is formed between the nodes N1 of the first main plate 21, which vibrate to a small extent, and the side plate 23. Similarly, the first holes 71D are formed between the nodes N1 of the first main plate 21, which do not vibrate, and the side plate 23.

The first recess 61D and the first holes 71D overlap each other in a plan view. For example, the first recess 61D has a width (dimension in the radial direction from the center) that is substantially the same as or larger than the diameter of the first holes 71D.

Also in this structure, air resistance between the first main plate 21 and the second main plate 22 decreases, and displacement of the first main plate 21 increases when the fluid control device 10D is in operation. This structure can thus increase the flow capacity, and improves the performance of the fluid control device 10D.

Sixth Embodiment

Figure 10:
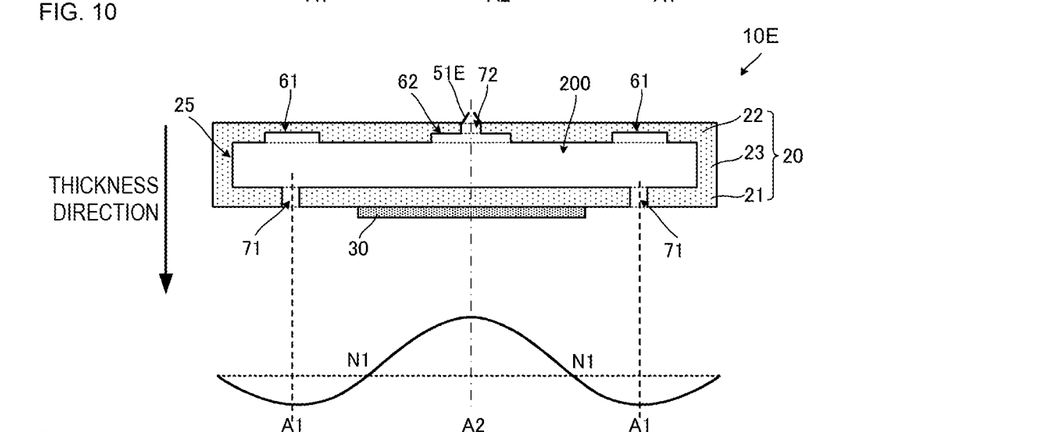
FIG. 10 is a cross-sectional view of a fluid control device 10E according to a sixth embodiment of the present disclosure, viewed sideways, in a bending vibration state.

A fluid control device according to a sixth embodiment of the present disclosure will be described with reference to the drawings. FIG. 10 is a cross-sectional view of a fluid control device 10E according to the sixth embodiment of the present disclosure, viewed sideways. For ease of illustration, some reference signs are omitted, and some components are exaggerated.

As illustrated in FIG. 10, the fluid control device 10E according to the sixth embodiment differs from the fluid control device 10 according to the first embodiment in that a valve unit 51E is disposed at a position different from that of the corresponding unit according to the first embodiment, and the valve unit 51E has a different structure. Other components of the fluid control device 10E are the same as those of the fluid control device 10, and will not be described. The fluid control device 10E according to the present embodiment is a pump.

The valve unit 51E is disposed at the second hole 72 on the side away from the pump chamber 200 in the second main plate 22, that is, on the outer side of the housing 20.

Also in this structure, air resistance between the first main plate 21 and the second main plate 22 decreases and displacement of the first main plate 21 increases when the fluid control device 10E is in operation. This structure can thus increase the flow capacity, and improves the performance of the fluid control device 10E.

Seventh Embodiment

Figure 11:
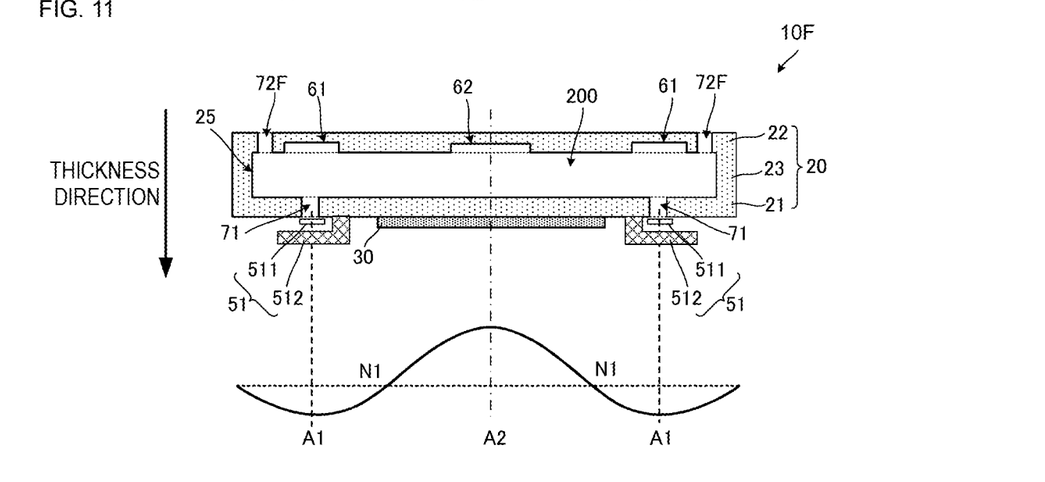
FIG. 11 is a cross-sectional view of a fluid control device 10F according to a seventh embodiment of the present disclosure, viewed sideways, in a bending vibration state.
Figure 12:
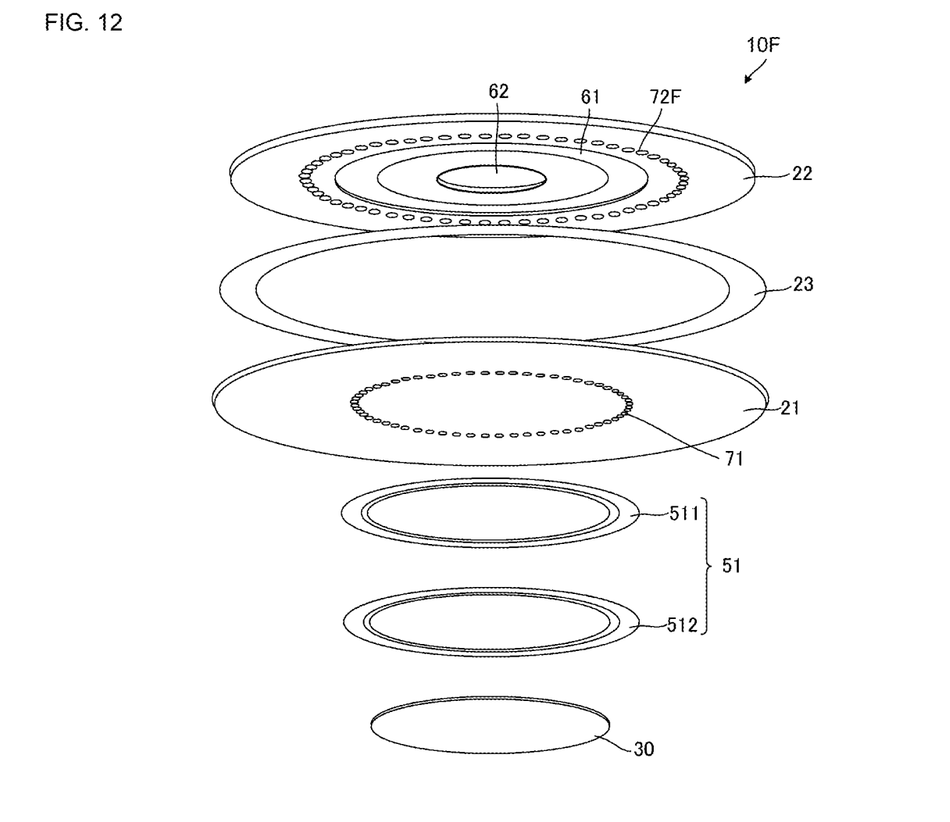
FIG. 12 is an exploded perspective view of the fluid control device 10F according to the seventh embodiment of the present disclosure.

A fluid control device according to a seventh embodiment of the present disclosure will be described with reference to the drawings. FIG. 11 is a cross-sectional view of a fluid control device 10F according to the seventh embodiment of the present disclosure, viewed sideways. FIG. 12 is an exploded perspective view of the fluid control device 10F according to the seventh embodiment of the present disclosure. For ease of illustration, some reference signs are omitted, and some components are exaggerated.

As illustrated in FIG. 11 and FIG. 12, the fluid control device 10F according to the seventh embodiment differs from the fluid control device 10 according to the first embodiment in that second holes 72F are formed at positions different from those of the corresponding holes according to the first embodiment. Other components of the fluid control device 10F are the same as those of the fluid control device 10, and will not be described.

The second holes 72F are formed between the first recess 61 and the circumference 25 in a plan view. The multiple second holes 72F are annularly arranged in the second main plate 22.

Also in this structure, air resistance between the first main plate 21 and the second main plate 22 decreases, and displacement of the first main plate 21 increases when the fluid control device 10F is in operation. This structure can thus increase the flow capacity, and improves the performance of the fluid control device 10F.

Eighth Embodiment

A fluid control device according to an eighth embodiment of the present disclosure will be described with reference to the drawings. FIG. 13A to FIG. 13E are cross-sectional views of the fluid control device according to the eighth embodiment of the present disclosure in a bending vibration state, viewed sideways. For ease of illustration, some reference signs are omitted, and some components are exaggerated.

Figure 13A:
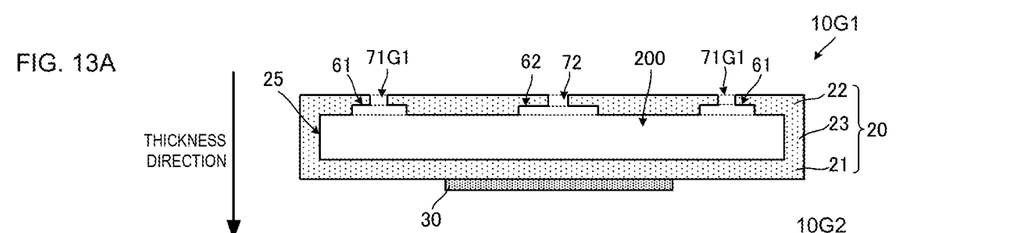
FIG. 13A to FIG. 13E are cross-sectional views of a fluid control device according to an eighth embodiment of the present disclosure, viewed sideways, in a bending vibration state.

As illustrated in FIG. 13A, a fluid control device 10G1 according to the eighth embodiment differs from the fluid control device 10 according to the first embodiment in that first holes 71G1 are formed at positions different from those of the corresponding holes according to the first embodiment, and the valve unit 51 is disposed at neither the first holes 71G1 nor the second hole 72. Other components of the fluid control device 10G1 are the same as those of the fluid control device 10, and will not be described.

The first holes 71G1 extend through the second main plate 22. The first holes 71G1 are formed to overlap the first recess 61, in a plan view. Each of the first holes 71G1 and the first recess 61 share the same center. The multiple first holes 71G1 are annularly arranged in the second main plate 22.

In the fluid control device 10G1, a valve may be disposed at neither the first holes 71G1 nor the second hole 72. Thus, the fluid control device 10G1 can discharge a jet through the first holes 71G1 with a synthetic jet effect.

The fluid control device 10G1 can cool a heat-producing component or control flow separation. As the maximum instantaneous flow capacity of a jet increases, a jet with a larger momentum can be obtained. Also in this structure, the momentum of a jet discharged through the first holes 71G1 can be increased.

Figure 13B:
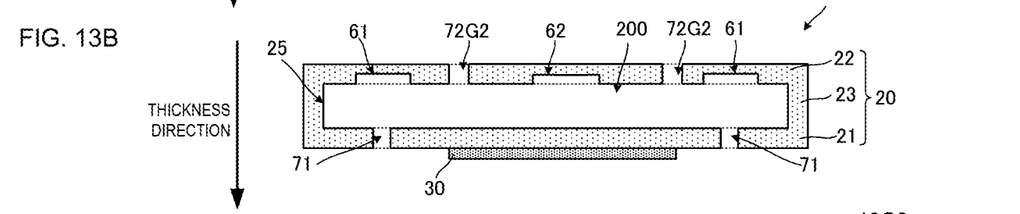

As illustrated in FIG. 13B, a fluid control device 10G2 according to the eighth embodiment differs from the fluid control device 10 according to the first embodiment in that second holes 72G2 are formed at positions different from those of the corresponding holes according to the first embodiment, and the valve unit 51 is disposed at neither the first holes 71 nor the second holes 72G2. Other components of the fluid control device 10G2 are the same as those of the fluid control device 10, and will not be described.

The second holes 72G2 extend through the second main plate 22. The second holes 72G2 are formed between the first recess 61 and the second recess 62 when the fluid control device 10G2 is viewed in a plan. The second holes 72G2 can overlap the nodes N1 in a plan view. The nodes N1 are displaced to a small extent, and thus the second holes 72G2 allow only a small amount of air to leak therethrough. Thus, air flow can be concentrated at the first holes 71, and the momentum of a jet increases.

In the fluid control device 10G2, a valve may be disposed at neither the first holes 71 nor the second holes 72G2. Thus, the fluid control device 10G2 can discharge a jet through the first holes 71 with a synthetic jet effect.

The fluid control device 10G2 can cool a heat-producing component and control flow separation. As the maximum instantaneous flow capacity of a jet increases, a jet with a larger momentum can be obtained. Also in this structure, the momentum of a jet discharged through the first holes 71 can be increased.

Figure 13C:
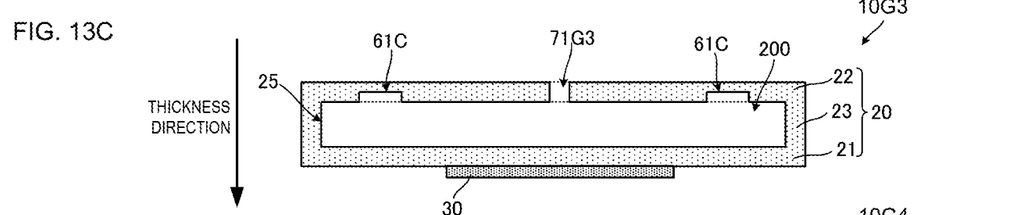

As illustrated in FIG. 13C, a fluid control device 10G3 according to an eighth embodiment differs from the fluid control device 10 according to the first embodiment in that the fluid control device 10G3 has neither the first holes 71 nor the second recess 62, and the valve unit 51 is not disposed at a second hole 71G3. Other components of the fluid control device 10G3 are the same as those of the fluid control device 10, and will not be described.

A first hole 71G3 extends through the second main plate 22. The first hole 71G3 and the housing 20 share the same center.

This structure can also discharge a jet through the first hole 71G3 with a synthetic jet effect. The fluid control device 10G3 can cool a heat-producing component or control flow separation. As the maximum instantaneous flow capacity of a jet increases, a jet with a larger momentum can be obtained. The fluid control device 10G3 with the structure according to the present disclosure can also increase the momentum of a jet discharged through the first hole 71G3.

Figure 13D:
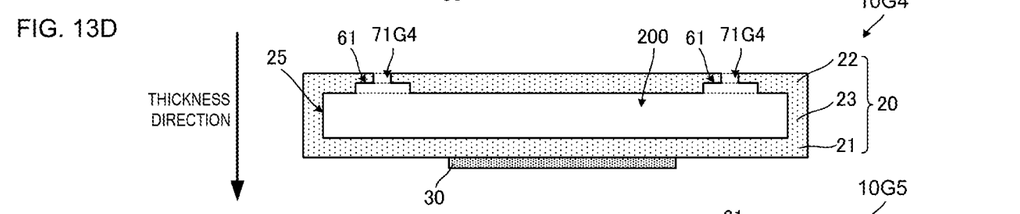

As illustrated in FIG. 13D, a fluid control device 10G4 according to the eighth embodiment differs from the fluid control device 10 according to the first embodiment in that first holes 71G4 are formed at positions different from those of the corresponding holes according to the first embodiment, and the fluid control device 10G4 has neither the second recess 62, the second hole 72, nor the valve unit 51. Other components of the fluid control device 10G4 are the same as those of the fluid control device 10, and will not be described.

The first holes 71G4 extend through the second main plate 22. The first holes 71G4 are formed to overlap the first recess 61 in a plan view. Each of the first holes 71G4 and the first recess 61 share the same center. The multiple first holes 71G4 are annularly arranged in the second main plate 22.

This structure can also discharge a jet through the first holes 71G4 with a synthetic jet effect. The fluid control device 10G4 can cool a heat-producing component or control flow separation. As the maximum instantaneous flow capacity of a jet increases, a jet with a larger momentum can be obtained. The fluid control device 10G4 with the structure according to the present disclosure can also increase the momentum of a jet discharged through the first holes 71G4.

Figure 13E:
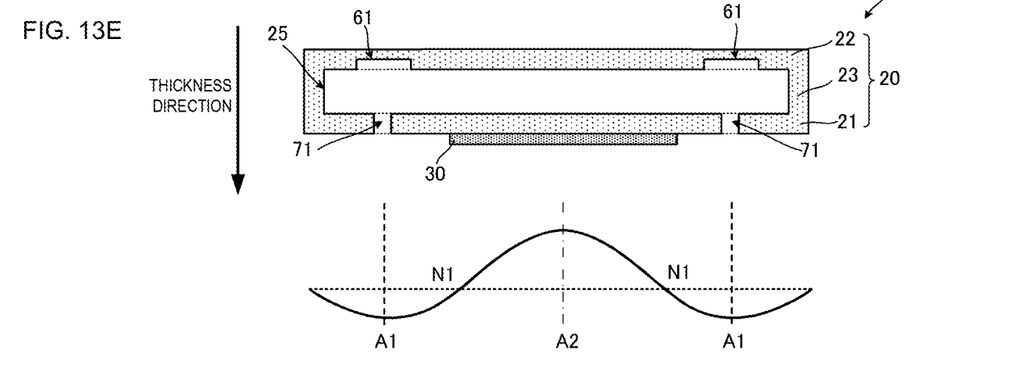

As illustrated in FIG. 13E, a fluid control device 10G5 according to the eighth embodiment differs from the fluid control device 10 according to the first embodiment in that the fluid control device 10G5 has neither the second recess 62, the second hole 72, nor the valve unit 51. Other components of the fluid control device 10G5 are the same as those of the fluid control device 10, and will not be described.

This structure can also discharge a jet through the first holes 71G5 with a synthetic jet effect. The fluid control device can cool a heat-producing component or control flow separation. As the maximum instantaneous flow capacity of a jet increases, a jet with a larger momentum can be obtained. The fluid control device 10G5 with a structure according to the present disclosure can also increase the momentum of a jet discharged through the first holes 71G5.

Each of the above embodiments has a structure where the first recess is formed in a full circle. However, a structure where the first recess is omitted in some area can also obtain an effect similar to the effect of each embodiment.

The present disclosure is not limited to the above embodiments, and may also include a combination of any two or more of these embodiments.

REFERENCE SIGNS LIST

A1, A2 antinode
N1 node
10, 10A, 10B, 10C, 10D, 10E, 10F, 10G1, 10G2, 10G3, 10G4, 10G5 fluid control device
20 housing
21 first main plate
22 second main plate
23 side plate
25 circumference
30 piezoelectric element
51, 51E valve unit
61, 61B, 61C, 61D first recess
62 second recess
71, 71B, 71D, 71G1, 71G3, 71G4 first hole
72, 72A, 72B, 72C, 72D, 72F, 72G, 72G2, 72G3 second hole
200 pump chamber
511 film
512 cover

The invention claimed is:

1. A fluid control device, comprising: a housing including: a first main plate, a second main plate having a first main surface opposing a first main surface of the first main plate, a side plate that connects the first main plate and the second main plate, and a pump chamber defined by the first main plate, the second main plate, and the side plate; a driver on either the first main surface or a second main surface of the first main plate to bend and vibrate the first main plate; a first hole that extends through the first main plate from the first main surface to the second main surface, or extends through the second main plate from the first main surface to the second main surface; and a first recess facing the pump chamber and extending partially through at least one of the first main plate offset from a center and a circumference, and the second main plate offset from the center and the circumference.

2. The fluid control device according to claim 1, further comprising:
   a second hole that extends through the first main plate or the second main plate from the first main surface to the second main surface; and
   a valve at the first hole.

3. The fluid control device according to claim 1,
   wherein the first recess is in the first main surface of the first main plate between the driver and the circumference or in the first main surface of the second main plate between the driver and the circumference.

4. The fluid control device according to claim 1,
wherein bending vibrations of the first main plate have a node of vibrations at a portion between the center and the circumference, and
wherein the first recess is between the node of vibrations and the circumference when the first main plate or the second main plate is viewed in a plan from the main surface of the first main plate to the main surface of the second main plate.

5. The fluid control device according to claim 4,
wherein bending vibrations of the first main plate have an antinode of vibrations between the node of vibrations and the circumference,
wherein the first recess overlaps an adjacent antinode of vibrations when the first main plate or the second main plate is viewed in a plan from the main surface of the first main plate to the main surface of the second main plate.

6. The fluid control device according to claim 1,
wherein the first hole overlaps the first recess when viewed in a plan from the main surface of the first main plate to the main surface of the second main plate.

7. The fluid control device according to claim 6,
wherein the first hole is in the main surface of the first main plate or the second main plate facing the first recess.

8. The fluid control device according to claim 1, wherein the first recess is in the second main plate.

9. The fluid control device according to claim 1, wherein the first recess has an annular form in the first main plate or the second main plate when viewed in a plan from the main surface of the first main plate to the main surface of the second main plate.

10. The fluid control device according to claim 1, wherein the first recess is a full circle in the first main plate or the second main plate.

11. The fluid control device according to claim 1, wherein a second recess is in the first main plate or the second main plate at a position corresponding to a center of the pump chamber.

12. The fluid control device according to claim 1, further comprising:
a second recess overlaps the first hole in a plan view.

13. The fluid control device according to claim 1, wherein the main surfaces of the first main plate and the main surfaces the second main plate are circular.

14. A medical device, comprising:
the fluid control device according to claim 1.

15. The fluid control device according to claim 2,
wherein the first recess is in the first main surface of the first main plate between the driver and the circumference or in the first main surface of the second main plate between the driver and the circumference.

16. The fluid control device according to claim 2,
wherein bending vibrations of the first main plate have a node of vibrations at a portion between the center and the circumference, and
wherein the first recess is between the node of vibrations and the circumference when the first main plate or the second main plate is viewed in a plan from the main surface of the first main plate to the main surface of the second main plate.

17. The fluid control device according to claim 2,
wherein the first hole overlaps the first recess when viewed in a plan from the main surface of the first main plate to the main surface of the second main plate.

18. The fluid control device according to claim 3,
wherein the first hole overlaps the first recess when viewed in a plan from the main surface of the first main plate to the main surface of the second main plate.

19. The fluid control device according to claim 4,
wherein the first hole overlaps the first recess when viewed in a plan from the main surface of the first main plate to the main surface of the second main plate.

20. The fluid control device according to claim 5,
wherein the first hole overlaps the first recess when viewed in a plan from the main surface of the first main plate to the main surface of the second main plate.

* * * * *

UNITED STATES PATENT AND TRADEMARK OFFICE
CERTIFICATE OF CORRECTION

PATENT NO. : 11,725,646 B2
APPLICATION NO. : 16/991403
DATED : August 15, 2023
INVENTOR(S) : Nobuhira Tanaka It is certified that error appears in the above-identified patent and that said Letters Patent is hereby corrected as shown below:

In the Claims

Claim 1, Column 14, Line 52, "a first recess" should be -- a first angular recess --; and Claim 1, Column 14, Line 56, please insert the following after "cumference" -- ; and wherein bending vibrations of the first main plate have a node of vibrations at a portion between the center and the circumstance; and wherein bending vibrations of the first main plate have an antinode of vibrations between the node of vibrations and the circumference. --.

Claim 4, Column 15, Lines 2-4, delete "wherein bending vibrations of the first main plate have a node of vibrations at a portion between the center and circumference,".

Claim 5, Column 15, Lines 11-13, delete "wherein bending vibrations of the first main plate have an antinode of vibrations between the node of vibrations and the circumference,".

Signed and Sealed this
Thirtieth Day of April, 2024

Katherine Kelly Vidal
*Director of the United States Patent and Trademark Office*